United States Patent [19]
Skatrud et al.

[11] Patent Number: 5,691,161
[45] Date of Patent: Nov. 25, 1997

[54] PEPTIDOGLYCAN BIOSYNTHETIC MURA PROTEIN FROM STREPTOCOCCUS PNEUMONIAE

[75] Inventors: Paul L. Skatrud, Indianapolis; Robert B. Peery, Brownsburg, both of Ind.

[73] Assignee: Eli Lilly and Company, Indianapolis, Ind.

[21] Appl. No.: 691,129

[22] Filed: Aug. 1, 1996

[51] Int. Cl.$^6$ .................................................. C12N 9/10
[52] U.S. Cl. .................................................. 435/15; 435/193
[58] Field of Search .................................................. 435/15, 193

[56] References Cited
PUBLICATIONS

Jacobs, M. R. (1992) Treatment and Diagnosis of Infections Caused by Drug-Resistant *Streptococcus pneumoniae*, Clin. Infect. Dis. 15: 119–127 Jan. 1992.

Ehrt, S. and Hillen, W. (1994) UDP-N-acetylglucosamine 1-carboxyvinyl-transferase from *Acinetobacter calcoaceticus* FEMS Microbiol. Lett. 117: 137–142 Jan. 1994.

Fleischmann, R. D. et al. (1995) Whole-Genome Random Sequencing and Assembly of *Haemophilus influenzae* Rd, Science 269: 496–512 Jul. 1995.

Wanke, C. et al. (1992) The UDP-N-acetylglucosamine 1-carboxyvinyl-transferase of *Enterobacter cloacae*, FEBS Letters 301: 271–276 Mar. 1992.

Trach K. et al. (1988) Complete Sequence and Transcriptional Analysis of the spoOF Region of the *Bacillus subtilis* Chromosome, J. Bacteriology 170: 4194–4208, Oct. 1988.

J. Marquardt et al. "Cloning and sequencing of *E. coli* murZ . . ." J. Bacter. 174, 5748–5752 (1992).

E. Brown et al. "MurA(MurZ), the enzyme that catalyzes the first committed step in peptidoglycan biosynthesis . . ." J. Bacter. 177, 4194–4197 (1995).

*Primary Examiner*—Robert A. Wax
*Assistant Examiner*—Einar Stole
*Attorney, Agent, or Firm*—Thomas D. Webster; David E. Boone

[57] ABSTRACT

The invention provides isolated nucleic acid compounds encoding the stem peptide biosynthetic gene murA of *Streptococcus pneumoniae*. Also provided are vectors and transformed heterologous host cells for expressing the MurA enzyme product and a method for identifying compounds that inhibit stem peptide biosynthesis.

5 Claims, 1 Drawing Sheet

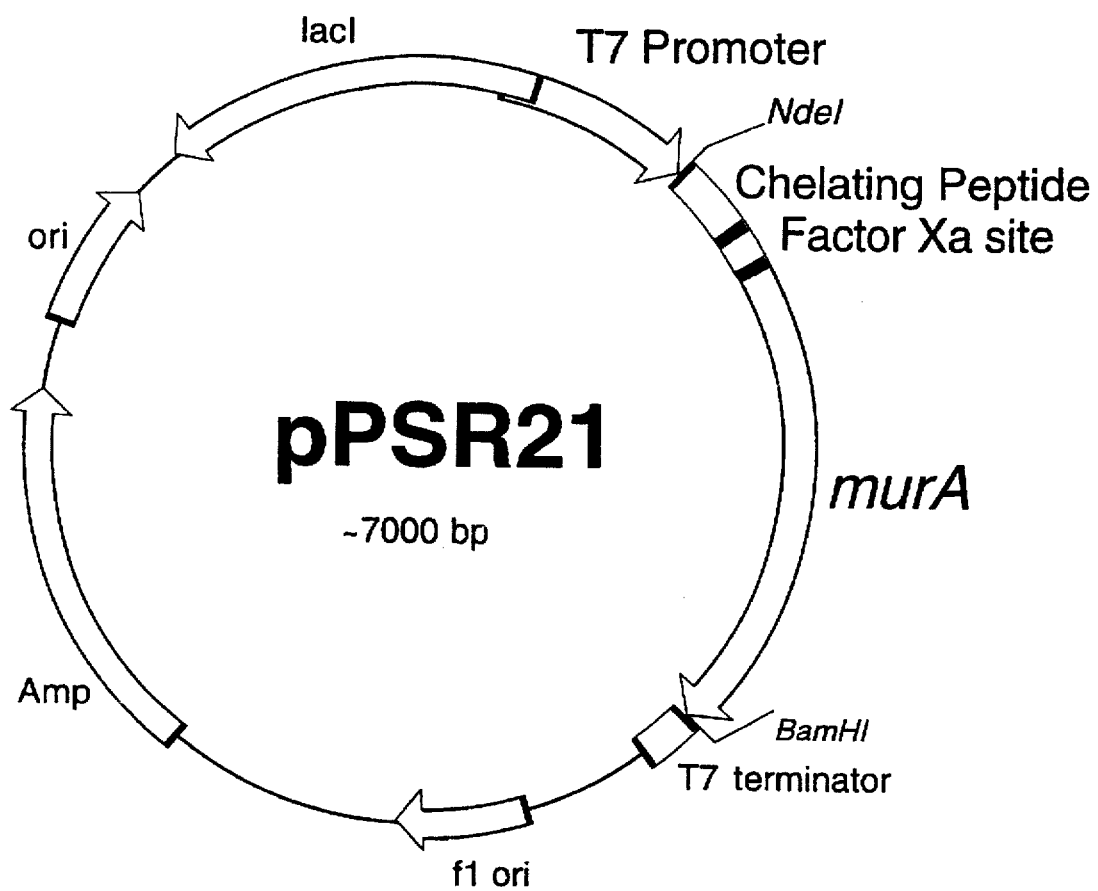

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1308 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1308

( x i ) SEQUENCE DESCRIPTION: SEQ ID NO:1:

```
ATG AAA TCA AGA GTA AAG GAA ACG AGT ATG GAT AAA ATT GTG GTT CAA        48
Met Lys Ser Arg Val Lys Glu Thr Ser Met Asp Lys Ile Val Val Gln
 1               5                  10                  15

GGT GGC GAT AAT CGT CTG GTA GGA AGC GTG ACG ATC GAG GGA GCA AAA        96
Gly Gly Asp Asn Arg Leu Val Gly Ser Val Thr Ile Glu Gly Ala Lys
             20                  25                  30

AAT GCA GTC TTA CCC TTG TTG GCA GCG ACT ATT CTA GCA AGT GAA GGA       144
Asn Ala Val Leu Pro Leu Leu Ala Ala Thr Ile Leu Ala Ser Glu Gly
         35                  40                  45

AAG ACC GTC TTG CAG AAT GTT CCG ATT TTG TCG GAT GTC TTT ATT ATG       192
Lys Thr Val Leu Gln Asn Val Pro Ile Leu Ser Asp Val Phe Ile Met
     50                  55                  60

AAT CAG GTA GTT GGT GGT TTG AAT GCC AAG GTT GAC TTT GAT GAG GAA       240
Asn Gln Val Val Gly Gly Leu Asn Ala Lys Val Asp Phe Asp Glu Glu
 65                  70                  75                  80
```

```
GCT CAT CTT GTC AAG GTG GAT GCT ACT GGC GAC ATC ACT GAG GAA GCC      288
Ala His Leu Val Lys Val Asp Ala Thr Gly Asp Ile Thr Glu Glu Ala
            85              90              95

CCT TAC AAG TAT GTC AGC AAG ATG CGC GCC TCC ATC GTT GTA TTA GGG      336
Pro Tyr Lys Tyr Val Ser Lys Met Arg Ala Ser Ile Val Val Leu Gly
            100             105             110

CCA ATC CTT GCC CGT GTG GGT CAT GCC AAG GTA TCC ATG CCA GGT GGT      384
Pro Ile Leu Ala Arg Val Gly His Ala Lys Val Ser Met Pro Gly Gly
            115             120             125

TGT ACG ATT GGT AGC CGT CCT ATT GAT CTT CAT TTG AAA GGT CTG GAA      432
Cys Thr Ile Gly Ser Arg Pro Ile Asp Leu His Leu Lys Gly Leu Glu
    130             135             140

GCT ATG GGG GTT AAG ATT AGT CAG ACA GCT GGT TAC ATC GAA GCC AAG      480
Ala Met Gly Val Lys Ile Ser Gln Thr Ala Gly Tyr Ile Glu Ala Lys
145             150             155             160

GCA GAA CGC TTG CAT GGC GCT CAT ATC TAT ATG GAC TTT CCA AGT GTT      528
Ala Glu Arg Leu His Gly Ala His Ile Tyr Met Asp Phe Pro Ser Val
                165             170             175

GGT GCA ACG CAG AAC TTG ATG ATG GCA GCG ACT CTG GCT GAT GGG GTG      576
Gly Ala Thr Gln Asn Leu Met Met Ala Ala Thr Leu Ala Asp Gly Val
            180             185             190

ACA GTG ATT GAG AAT GCT GCG CGT GAG CCT GAG ATT GTT GAC TTA GCC      624
Thr Val Ile Glu Asn Ala Ala Arg Glu Pro Glu Ile Val Asp Leu Ala
            195             200             205

ATT CTC CTT AAT GAA ATG GGA GCC AAG GTC AAA GGT GCT GGT ACA GAG      672
Ile Leu Leu Asn Glu Met Gly Ala Lys Val Lys Gly Ala Gly Thr Glu
    210             215             220

ACT ATA ACC ATT ACT GGT GTT GAG AAA CTT CAT GGT ACG ACT CAC AAT      720
Thr Ile Thr Ile Thr Gly Val Glu Lys Leu His Gly Thr Thr His Asn
225             230             235             240

GTA GTC CAA GAC CGT ATC GAA GCA GGA ACC TTT ATG GTA GCT GCT GCC      768
Val Val Gln Asp Arg Ile Glu Ala Gly Thr Phe Met Val Ala Ala Ala
                245             250             255

ATG ACT GGT GGT GAT GTC TTG ATT CGA GAC GCT GTC TGG GAG CAC AAC      816
Met Thr Gly Gly Asp Val Leu Ile Arg Asp Ala Val Trp Glu His Asn
            260             265             270

CGT CCC TTG ATT GCC AAG TTA CTT GAA ATG GGT GTT GAA GTA ATT GAA      864
Arg Pro Leu Ile Ala Lys Leu Leu Glu Met Gly Val Glu Val Ile Glu
            275             280             285

GAA GAC GAA GGA ATT CGT GTT CGT TCT CAA CTA GAA AAT CTA AAA GCT      912
Glu Asp Glu Gly Ile Arg Val Arg Ser Gln Leu Glu Asn Leu Lys Ala
    290             295             300

GTT CAT GTG AAA ACC TTG CCC CAC CCA GGA TTT CCA ACA GAT ATG CAG      960
Val His Val Lys Thr Leu Pro His Pro Gly Phe Pro Thr Asp Met Gln
305             310             315             320

GCT CAA TTT ACA GCC TTG ATG ACA GTT GCA AAA GGC GAA TCA ACC ATG     1008
Ala Gln Phe Thr Ala Leu Met Thr Val Ala Lys Gly Glu Ser Thr Met
                325             330             335

GTG GAG ACA GTT TTC GAA AAT CGT TTC CAA CAC CTA GAA GAG ATG CGC     1056
Val Glu Thr Val Phe Glu Asn Arg Phe Gln His Leu Glu Glu Met Arg
            340             345             350

CGC ATG GGC TTG CAT TCT GAG ATT ATC CGT GAT ACA GCT CGT ATT GTT     1104
Arg Met Gly Leu His Ser Glu Ile Ile Arg Asp Thr Ala Arg Ile Val
            355             360             365

GGT GGA CAG CCT TTG CAG GGA GCA GAA GTT CTT TCA ACT GAC CTT CGT     1152
Gly Gly Gln Pro Leu Gln Gly Ala Glu Val Leu Ser Thr Asp Leu Arg
    370             375             380

GCC AGT GCA GCC TTG ATT TTG ACA GGT TTG GTA GCA CAG GGA GAA ACT     1200
Ala Ser Ala Ala Leu Ile Leu Thr Gly Leu Val Ala Gln Gly Glu Thr
385             390             395             400
```

```
GTG  GTC  GGT  AAA  TTG  GTT  CAC  TTG  GAT  AGA  GGT  TAC  TAC  GGT  TTC  CAT          1248
Val  Val  Gly  Lys  Leu  Val  His  Leu  Asp  Arg  Gly  Tyr  Tyr  Gly  Phe  His
                         405                     410                     415

GAG  AAG  TTG  GCG  CAG  CTA  GGT  GCT  AAG  ATT  CAG  CGG  ATT  GAG  GCA  AAT          1296
Glu  Lys  Leu  Ala  Gln  Leu  Gly  Ala  Lys  Ile  Gln  Arg  Ile  Glu  Ala  Asn
                         420                     425                     430

GAT  GAA  GAT  GAA                                                                       1308
Asp  Glu  Asp  Glu
               435
```

(2) INFORMATION FOR SEQ ID NO:2:

(i) SEQUENCE CHARACTERISTICS:
        (A) LENGTH: 436 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Lys  Ser  Arg  Val  Lys  Glu  Thr  Ser  Met  Asp  Lys  Ile  Val  Val  Gln
 1                   5                   10                       15

Gly  Gly  Asp  Asn  Arg  Leu  Val  Gly  Ser  Val  Thr  Ile  Glu  Gly  Ala  Lys
               20                        25                   30

Asn  Ala  Val  Leu  Pro  Leu  Leu  Ala  Thr  Ile  Leu  Ala  Ser  Glu  Gly
          35                        40                   45

Lys  Thr  Val  Leu  Gln  Asn  Val  Pro  Ile  Leu  Ser  Asp  Val  Phe  Ile  Met
     50                        55                   60

Asn  Gln  Val  Val  Gly  Gly  Leu  Asn  Ala  Lys  Val  Asp  Phe  Asp  Glu  Glu
65                        70                   75                            80

Ala  His  Leu  Val  Lys  Val  Asp  Ala  Thr  Gly  Asp  Ile  Thr  Glu  Glu  Ala
               85                        90                   95

Pro  Tyr  Lys  Tyr  Val  Ser  Lys  Met  Arg  Ala  Ser  Ile  Val  Val  Leu  Gly
               100                      105                  110

Pro  Ile  Leu  Ala  Arg  Val  Gly  His  Ala  Lys  Val  Ser  Met  Pro  Gly  Gly
          115                      120                      125

Cys  Thr  Ile  Gly  Ser  Arg  Pro  Ile  Asp  Leu  His  Leu  Lys  Gly  Leu  Glu
     130                      135                      140

Ala  Met  Gly  Val  Lys  Ile  Ser  Gln  Thr  Ala  Gly  Tyr  Ile  Glu  Ala  Lys
145                      150                      155                       160

Ala  Glu  Arg  Leu  His  Gly  Ala  His  Ile  Tyr  Met  Asp  Phe  Pro  Ser  Val
               165                      170                      175

Gly  Ala  Thr  Gln  Asn  Leu  Met  Met  Ala  Ala  Thr  Leu  Ala  Asp  Gly  Val
               180                      185                      190

Thr  Val  Ile  Glu  Asn  Ala  Ala  Arg  Glu  Pro  Glu  Ile  Val  Asp  Leu  Ala
          195                      200                      205

Ile  Leu  Leu  Asn  Glu  Met  Gly  Ala  Lys  Val  Lys  Gly  Ala  Gly  Thr  Glu
     210                      215                      220

Thr  Ile  Thr  Ile  Thr  Gly  Val  Glu  Lys  Leu  His  Gly  Thr  Thr  His  Asn
225                      230                      235                       240

Val  Val  Gln  Asp  Arg  Ile  Glu  Ala  Gly  Thr  Phe  Met  Val  Ala  Ala  Ala
               245                      250                      255

Met  Thr  Gly  Gly  Asp  Val  Leu  Ile  Arg  Asp  Ala  Val  Trp  Glu  His  Asn
               260                      265                      270

Arg  Pro  Leu  Ile  Ala  Lys  Leu  Leu  Glu  Met  Gly  Val  Glu  Val  Ile  Glu
          275                      280                      285

Glu  Asp  Glu  Gly  Ile  Arg  Val  Arg  Ser  Gln  Leu  Glu  Asn  Leu  Lys  Ala
```

|          |       |     |     |     | 290 |     |     |     |     | 295 |     |     |     |     | 300 |     |     |     |     |
|----------|-------|-----|-----|-----|-----|-----|-----|-----|-----|-----|-----|-----|-----|-----|-----|-----|-----|-----|-----|

```
Val   His   Val   Lys   Thr   Leu   Pro   His   Pro   Gly   Phe   Pro   Thr   Asp   Met   Gln
305                           310                     315                           320
Ala   Gln   Phe   Thr   Ala   Leu   Met   Thr   Val   Ala   Lys   Gly   Glu   Ser   Thr   Met
                        325                     330                           335
Val   Glu   Thr   Val   Phe   Glu   Asn   Arg   Phe   Gln   His   Leu   Glu   Glu   Met   Arg
                  340                     345                           350
Arg   Met   Gly   Leu   His   Ser   Glu   Ile   Ile   Arg   Asp   Thr   Ala   Arg   Ile   Val
            355                     360                           365
Gly   Gly   Gln   Pro   Leu   Gln   Gly   Ala   Glu   Val   Leu   Ser   Thr   Asp   Leu   Arg
      370                     375                           380
Ala   Ser   Ala   Ala   Leu   Ile   Leu   Thr   Gly   Leu   Val   Ala   Gln   Gly   Glu   Thr
385                     390                           395                           400
Val   Val   Gly   Lys   Leu   Val   His   Leu   Asp   Arg   Gly   Tyr   Tyr   Gly   Phe   His
                  405                     410                           415
Glu   Lys   Leu   Ala   Gln   Leu   Gly   Ala   Lys   Ile   Gln   Arg   Ile   Glu   Ala   Asn
                  420                     425                           430
Asp   Glu   Asp   Glu
                  435
```

( 2 ) INFORMATION FOR SEQ ID NO:3:

( i ) SEQUENCE CHARACTERISTICS:
        ( A ) LENGTH: 1308 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

```
AUGAAAUCAA GAGUAAAGGA AACGAGUAUG GAUAAAUUG  UGGUUCAAGG UGGCGAUAAU       60
CGUCUGGUAG GAAGCGUGAC GAUCGAGGGA GCAAAAAUG  CAGUCUUACC CUUGUUGGCA      120
GCGACUAUUC UAGCAAGUGA AGGAAAGACC GUCUUGCAGA AUGUUCCGAU UUUGUCGGAU      180
GUCUUUAUUA UGAAUCAGGU AGUUGGUGGU UUGAAUGCCA AGGUUGACUU UGAUGAGGAA      240
GCUCAUCUUG UCAAGGUGGA UGCUACUGGC GACAUCACUG AGGAAGCCCC UUACAAGUAU      300
GUCAGCAAGA UGCGCGCCUC CAUCGUUGUA UUAGGGCCAA UCCUUGCCCG UGUGGGUCAU      360
GCCAAGGUAU CCAUGCCAGG UGGUUGUACG AUUGGUAGCC GUCCUAUUGA UCUUCAUUUG      420
AAAGGUCUGG AAGCUAUGGG GGUUAAGAUU AGUCAGACAG CUGGUUACAU CGAAGCCAAG      480
GCAGAACGCU UGCAUGGCGC UCAUACUAU  AUGGACUUUC CAAGUGUUGG UGCAACGCAG      540
AACUUGAUGA UGGCAGCGAC UCUGGCUGAU GGGGUGACAG UGAUUGAGAA UGCUGCGCGU      600
GAGCCUGAGA UUGUUGACUU AGCCAUUCUC CUUAAUGAAA UGGGAGCCAA GGUCAAAGGU      660
GCUGGUACAG AGACUAUAAC CAUUACUGGU GUUGAGAAAC UUCAUGGUAC GACUCACAAU      720
GUAGUCCAAG ACCGUAUCGA AGCAGGAACC UUUAUGGUAG CUGCUGCCAU GACUGGUGGU      780
GAUGUCUUGA UUCGAGACGC UGUCUGGGAG CACAACCGUC CCUUGAUUGC CAAGUUACUU      840
GAAAUGGGUG UUGAAGUAAU UGAAGAAGAC GAAGGAAUUC GUGUUCGUUC UCAACUAGAA      900
AAUCUAAAAG CUGUUCAUGU GAAAACCUUG CCCCACCCAG GAUUUCCAAC AGAUAUGCAG      960
GCUCAAUUUA CAGCCUUGAU GACAGUUGCA AAAGGCGAAU CAACCAUGGU GGAGACAGUU     1020
```

-continued

| | | | | | | |
|---|---|---|---|---|---|---|
| UUCGAAAAUC | GUUUCCAACA | CCUAGAAGAG | AUGCGCCGCA | UGGGCUUGCA | UUCUGAGAUU | 1080 |
| AUCCGUGAUA | CAGCUCGUAU | UGUUGGUGGA | CAGCCUUUGC | AGGGAGCAGA | AGUUCUUUCA | 1140 |
| ACUGACCUUC | GUGCCAGUGC | AGCCUUGAUU | UUGACAGGUU | UGGUAGCACA | GGGAGAAACU | 1200 |
| GUGGUCGGUA | AAUUGGUUCA | CUUGGAUAGA | GGUUACUACG | GUUUCCAUGA | GAAGUUGGCG | 1260 |
| CAGCUAGGUG | CUAAGAUUCA | GCGGAUUGAG | GCAAAUGAUG | AAGAUGAA | | 1308 |

PEPTIDOGLYCAN BIOSYNTHETIC MURA PROTEIN FROM *STREPTOCOCCUS PNEUMONIAE*

BACKGROUND OF THE INVENTION

This invention relates to recombinant DNA technology. In particular the invention pertains to the cloning of the murA gene encoding UDPGlcNAc enolpyruvyl transferase of *Streptococcus pneumoniae* and the use of the murA gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that compounds that interfere with cell wall biosynthesis have low toxicity in humans and potentially high therapeutic value.

The bacterial cell wall structure contains a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is the peptidoglycan crosslinking step that has been a frequently targeted site for antibiotic compounds such as the beta-lactam antibiotics.

Unlike the widely targeted peptidoglycan crosslinking step, the stem peptide pathway has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by UDP-N-acetylmuramate:L-alanine ligase; UDP-N-acetyl-muramyl-L-alanine:D-glutamate ligase; UDP-N-acetyl-muramyl-L-alanyl-D-isoglutamate:L-lysine ligase; UDP-N-acetylmuramyl-L-alanyl-D-isoglutamyl-L-lysine:D-alanyl-D-alanine ligase; and D-alanyl-D-alanine ligase, the final product, UDPMurNAc-L-Ala-D-isoGlu-L-lysine-D-Ala-D-Ala, is produced in *Streptococcus pneumoniae*.

The enzymatic steps involved in the formation of the stem peptide are potential targets for new antibacterial agents. A few inhibitors, which target this pathway, have been developed. For example, D-cycloserine inhibits alanine racemase and D-alanine-D-alanine ligase; phosphonomycin inhibits the conversion of UDP-GlcNAc to UDP-GlcNac-enolpyruvate; and Ala-phosphonine inhibits the formation of UDP-MurNac-L-Ala.

While inroads in the development of new antibiotics and new targets for antibiotic compounds have emerged in a variety of microorganisms, progress has been less apparent in *Streptococcus pneumoniae*. In part, *Streptococcus pneumoniae* presents a special case because this organism is highly mutagenic and readily takes up exogenous DNA from its surroundings. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the murA gene product from *Streptococcus pneumoniae*. The invention also provides the protein product of the *Streptococcus pneumoniae* murA gene, UDPGlcNAc enolpyruvyl transferase (MurA protein), in substantially purified form.

Having the cloned murA gene of *Streptococcus pneumoniae* enables the production of recombinant MurA protein and the implementation of large scale screens to identify new inhibitory compounds targeted at the stem peptide biosynthetic pathway. It may be possible to combine stem peptide proteins in a single screen to examine several steps at the same time. Structural analysis of the MurA protein will enable structure-based drug design to develop novel compounds effective in the treatment of antibiotic resistant microorganisms.

In one embodiment the present invention relates to an isolated DNA molecule encoding MurA protein, said DNA molecule comprising the nucleotide sequence identified as SEQ ID NO. 1:

| | | | | | | |
|---|---|---|---|---|---|---|
| ATGAAATCAA | GAGTAAAGGA | AACGAGTATG | GATAAAATTG | TGGTTCAAGG | TGGCGATAAT | 60 |
| CGTCTGGTAG | GAAGCGTGAC | GATCGAGGGA | GCAAAAAATG | CAGTCTTACC | CTTGTTGGCA | 120 |
| GCGACTATTC | TAGCAAGTGA | AGGAAAGACC | GTCTTGCAGA | ATGTTCCGAT | TTTGTCGGAT | 180 |
| GTCTTTATTA | TGAATCAGGT | AGTTGGTGGT | TTGAATGCCA | AGGTTGACTT | TGATGAGGAA | 240 |
| GCTCATCTTG | TCAAGGTGGA | TGCTACTGGC | GACATCACTG | AGGAAGCCCC | TTACAAGTAT | 300 |
| GTCAGCAAGA | TGCGCGCCTC | CATCGTTGTA | TTAGGGCCAA | TCCTTGCCCG | TGTGGGTCAT | 360 |
| GCCAAGGTAT | CCATGCCAGG | TGGTTGTACG | ATTGGTAGCC | GTCCTATTGA | TCTTCATTTG | 420 |
| AAAGGTCTGG | AAGCTATGGG | GGTTAAGATT | AGTCAGACAG | CTGGTTACAT | CGAAGCCAAG | 480 |
| GCAGAACGCT | TGCATGGCGC | TCATATCTAT | ATGGACTTTC | CAAGTGTTGG | TGCAACGCAG | 540 |
| AACTTGATGA | TGGCAGCGAC | TCTGGCTGAT | GGGGTGACAG | TGATTGAGAA | TGCTGCGCGT | 600 |
| GAGCCTGAGA | TTGTTGACTT | AGCCATTCTC | CTTAATGAAA | TGGGAGCCAA | GGTCAAAGGT | 660 |
| GCTGGTACAG | AGACTATAAC | CATTACTGGT | GTTGAGAAAC | TTCATGGTAC | GACTCACAAT | 720 |
| GTAGTCCAAG | ACCGTATCGA | AGCAGGAACC | TTTATGGTAG | CTGCTGCCAT | GACTGGTGGT | 780 |
| GATGTCTTGA | TTCGAGACGC | TGTCTGGGAG | CACAACCGTC | CCTTGATTGC | CAAGTTACTT | 840 |

-continued

| | | | | | | |
|---|---|---|---|---|---|---|
| GAAATGGGTG | TTGAAGTAAT | TGAAGAAGAC | GAAGGAATTC | GTGTTCGTTC | TCAACTAGAA | 900 |
| AATCTAAAAG | CTGTTCATGT | GAAAACCTTG | CCCCACCCAG | GATTTCCAAC | AGATATGCAG | 960 |
| GCTCAATTTA | CAGCCTTGAT | GACAGTTGCA | AAAGGCGAAT | CAACCATGGT | GGAGACAGTT | 1020 |
| TTCGAAAATC | GTTTCCAACA | CCTAGAAGAG | ATGCGCCGCA | TGGGCTTGCA | TTCTGAGATT | 1080 |
| ATCCGTGATA | CAGCTCGTAT | TGTTGGTGGA | CAGCCTTTGC | AGGGAGCAGA | AGTTCTTTCA | 1140 |
| ACTGACCTTC | GTGCCAGTGC | AGCCTTGATT | TTGACAGGTT | TGGTAGCACA | GGGAGAAACT | 1200 |
| GTGGTCGGTA | AATTGGTTCA | CTTGGATAGA | GGTTACTACG | GTTTCCATGA | GAAGTTGGCG | 1260 |
| CAGCTAGGTG | CTAAGATTCA | GCGGATTGAG | GCAAATGATG | AAGATGAA | | 1308 |

In another embodiment the present invention relates to a MurA protein molecule, wherein said protein molecule comprises the sequence identified as SEQ ID NO. 2.

In a further embodiment the present invention relates to a ribonucleic acid molecule encoding MurA protein, said ribonucleic acid molecule comprising the sequence identified as SEQ ID NO. 3:

In yet another embodiment, the present invention relates to a recombinant DNA vector which incorporates the Streptococcus pneumoniae murA gene in operable linkage to gene expression sequences enabling the murA gene to be transcribed and translated in a host cell.

In still another embodiment the present invention relates to homologous or heterologous host cells which have been transformed or transfected with the cloned murA gene of Streptococcus pneumoniae such that the murA gene is expressed in the host cell.

In a still further embodiment, the present invention relates to a method for identifying compounds that inhibit the enzymatic activity of the MurA protein of Streptococcus pneumoniae.

DESCRIPTION OF THE DRAWING

FIGURE. Plasmid pPSR21, useful for high level expression of the Streptococcus pneumoniae murA gene in the heterologous procaryotic host cell Eschericia coli.

Definitions

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"MurA" refers to the protein encoded by murA, UDPGlcNAc enolpyruvyl transferase.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

DETAILED DESCRIPTION

The murA gene of Streptococcus pneumoniae encodes an enzyme which catalyzes the first committed step in stem peptide biosynthesis. The stem peptide pathway is necessary for the synthesis of the peptidoglycan layer, which is part of the bacterial cell wall. There are at least 10 steps involved in stem peptide biosynthesis. The murA gene encodes UDPGlcNAc enolpyruvyl transferase (SEQ ID NO. 2), which catalyzes the transfer of the enolpyruvyl moiety of phosphoenolpyruvate (PEP) onto UDPGlcNAc.

The murA gene of *Streptococcus pneumoniae* comprises a DNA sequence of 1308 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the murA gene may be obtained by a plurality of applicable genetic and recombinant DNA techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the murA gene of *Streptococcus pneumoniae* or fragment thereof could be isolated by PCR amplification of *Streptococcus pneumoniae* genomic DNA or cDNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One embodiment of the present invention relates to the substantially purified protein encoded by the murA gene, or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably −20° C. for thirty minutes followed by thirty minutes at 0° C.

The protein of the present invention can also be produced by recombinant DNA methods using the cloned murA gene of *Streptococcus pneumoniae*. Recombinant methods are preferred if a high yield is desired. Expression of the cloned murA gene can be carried out in a variety of suitable host cells well known to those skilled in the art. The murA gene is introduced into a host cell by any suitable means, well known to those skilled in the art. While chromosomal integration of the cloned murA gene is within the scope of the present invention, it is preferred that the gene be cloned into a suitable extra-chromosomally maintained expression vector so that the coding region of the murA gene is operably linked to a constitutive or inducible promoter.

The basic steps in the recombinant production of the MurA protein are:

a) constructing a natural, synthetic or semi-synthetic DNA encoding MurA protein;

b) integrating said DNA into an expression vector in a manner suitable for expressing the MurA protein, either alone or as a fusion protein;

c) transforming or otherwise introducing said vector into an appropriate eucaryotic or prokaryotic host cell forming a recombinant host cell, d) culturing said recombinant host cell in a manner to express the MurA protein; and e) recovering and substantially purifying the MurA protein by any suitable means, well known to those skilled in the art.

Expressing Recombinant MurA Protein in Procaryotic and Eucaryotic Host Cells

In general, procaryotes are used for cloning DNA sequences and for constructing the vectors of the present invention. Procaryotes may also be employed in the production of the MurA protein. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed as host cells in the cloning and expression of the recombinant proteins of this invention.

Promoter sequences suitable for driving the expression of genes in procaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of mammalian cell systems and eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MurA Protein

An expression vector carrying the cloned murA gene of *Streptococcus pneumoniae* is transformed or transfected into a suitable host cell using standard methods. Cells which contain the vector are then propagated under conditions suitable for expression of the MurA protein. If the gene is under the control of an inducible promoter then suitable growth conditions would incorporate the appropriate inducer. The recombinantly-produced protein may be purified from cellular extracts of transformed cells by any suitable means.

In a preferred process for protein purification the murA gene is modified at the 5' end to incorporate several histidine residues at the amino terminus of the MurA protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure MurA protein starting from a crude cellular extract.

Other embodiments of the present invention comprise isolated nucleic acid sequences which encode SEQ ID NO: 2. As skilled artisans will recognize, the amino acid compounds of the invention can be encoded by a multitude of different nucleic acid sequences because most of the amino acids are encoded by more than one codon due to the degeneracy of the genetic code. Because these alternative nucleic acid sequences would encode the same amino acid sequences, the present invention further comprises these alternate nucleic acid sequences.

The murA gene, which comprises nucleic acid encoding SEQ ID NO: 2, may be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the murA gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative methodology, namely PCR, the murA DNA sequence comprising a portion or all of SEQ ID NO: 1 can be generated from *Streptococcus pneumoniae* genomic DNA using suitable oligonucleotide primers complementary to SEQ ID NO: 1 or region therein, as described in U.S. Pat. No. 4,889,818, which hereby is incorporated by reference. Suitable protocols for performing the PCR are disclosed in, for example, *PCR Protocols: A Guide to Method and Applications*, Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a murA DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO: 1 or SEQ ID NO:3.

The present invention also provides probes and primers useful for a variety of molecular biology techniques including, for example, hybridization screens of genomic or subgenomic libraries. A nucleic acid compound comprising SEQ ID NO: 1, SEQ ID NO: 3 or a complementary sequence thereof, or a fragment thereof, and which is at least 18 base pairs in length, and which will selectively hybridize to *Streptococcus pneumoniae* DNA or mRNA encoding murA, is provided. Preferably, the 18 or more base pair compound is DNA. A probe or primer length of at least 18 base pairs is dictated by theoretical and practical considerations. See e.g. B. Wallace and G. Miyada, "Oligonucleotide Probes for the Screening of Recombinant DNA Libraries," In *Methods in Enzymology*, Vol. 152, 432–442, Academic Press (1987).

These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO: 1. Plasmid pPSR21 is an especially preferred DNA vector of the present invention.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. The skilled artisan will recognize a number of inducible promoters which respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing the extra-cellular export of a resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO: 2, said method comprising transforming or otherwise introducing into a host cell a recombinant DNA vector that comprises an isolated DNA sequence which encodes SEQ ID NO: 2. The preferred host cell is any strain of *E. coli* which can accomodate high level expression of an exogenously introduced gene. Preferred vectors for expression are those which comprise SEQ ID NO: 1. An especially preferred expression vector for use in *E. coli* is plasmid pPSR21, which comprises SEQ ID NO: 1. (See FIGURE). Transformed host cells may be cultured under conditions well known to skilled artisans such that SEQ ID NO: 2 is expressed, thereby producing MurA protein in the recombinant host cell.

For the purpose of identifying or developing inhibitors of the stem peptide pathway, it would be desirable to determine those agents which inhibit the MurA step. A method for determining whether a substance will inhibit the enzymatic reaction catalyzed by the MurA protein comprises contacting the MurA protein with a test inhibitory compound and monitoring MurA enzyme activity by any suitable means.

The instant invention provides such a screening system useful for discovering compounds which inhibit the MurA protein, said screening system comprising the steps of:

a) preparing MurA enzyme;

b) exposing said MurA enzyme to a test inhibitor;

c) introducing a specific MurA substrate; and d) quantifying the loss of activity of said MurA enzyme.

Utilization of the screening system described above provides a means to determine compounds which interfere with stem peptide biosynthesis. This screening method may be adapted to automated procedures such as a PANDEX® (Baxter-Dade Diagnostics) system, allowing for efficient high-volume screening of potential therapeutic agents.

In such a screening protocol MurA enzyme is prepared as described herein, preferably using recombinant DNA technology. A test inhibitory compound is then introduced into the reaction vessel containing the MurA enzyme, followed by addition of enzyme substrate. Alternatively, substrate may be added simultaneously with the test compound. For example, in a preferred method radioactively or chemically-labeled substrate may be used. The products of the enzymatic reaction are assayed for the chemical label or radioactivity by any suitable means. The absence or diminution of the chemical label or radioactivity indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical arts.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Streptococcus pnuemoniae* murA Gene in a Homologous or Heterologous Host Plasmid pPSR21 (See FIGURE) is an approximately 7000 base pair expression vector suitable for expressing the murA gene of *S. pneumoniae* in the procaryotic host *E. coli*. This plasmid contains an origin of replication (Ori), an ampicillin resistance gene (Amp), useful for selecting cells which have incorporated the vector following a tranformation procedure, and further comprises the lacI gene for repression of the lac operon, as well as the T7 promoter and T7 terminator sequences in operable linkage to the coding region of the murA gene. Parent plasmid pET11A (obtained from Novogen, Madison, Wis.) was linearized by digestion with endonucleases NdeI and BamHI. Linearized pET11A was ligated to a DNA fragment bearing NdeI and BamHI sticky ends and further comprising the coding region of the *S. pneumoniae* murA gene.

The murA gene, which was ligated into pPSR21, was modified at the 5' end (amino terminus of encoded protein) in order to simplify purification of the encoded MurA protein product. For this purpose, an oligonucleotide encoding 8 histidine residues and a factor Xa cleavage site was inserted after the ATG start codon at nucleotide positions 1 to 3 of SEQ ID NO: 1. Placement of the histidine residues at the amino terminus of the encoded protein does not affect its activity and serves only to enable the IMAC one-step protein purification procedure (See below).

EXAMPLE 2

Expression of *Streptococcus pneumoniae* MurA Gene in *Echerichia coli* and Purification of MurA Enzyme Plasmid pPSR21 is transformed into *E. coli* BL21 (DE3) (hsdS gal λcIts857 indlSam7nin5lacUV5-T7gene 1) using standard methods (See e.g. Sambrook et al. Supra). Transformants, selected for resistance to ampicillin, are chosen at random and tested for the presence of pPSR21 by agarose gel electrophoresis using quick plasmid preparations. Id. Colonies that contain pPSR21 are grown, processed, and the protein product encoded by the murA gene purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract prepared from a recombinant host transformed or transfected with plasmid pPSR21.

After washing the column with a suitable buffer, pH 7.5 to remove unbound proteins and other materials, the bound recombinant MurA protein is eluted in a buffer at pH 4.3, essentially as described in U.S. Pat. No. 4,569,794.

EXAMPLE 3

BioChemical Assay for Inhibitors of *Streptococcus pneumoniae* MurA Enzyme Product The activity of the MurA enzyme is assayed by monitoring the UDP-GlcNAc-dependent release of $P_i$ from PEP. Seventy microliters of the test sample is added to 30 µl of mixture containing 10 µl of 250 mM Tris-HCl, pH 7.8, 10 µl of 100 mM UDP-GlcNAc, and 10 µl of 100 mM PEP. The reaction is incubated at 37° C. and the amount of $P_i$ released at varying times is assayed by the method of Lanzetta et al. Anal. Biochem. 100, 95–97 (1979).

Inhibition studies are carried out using the reaction conditions described in the preceding paragraph. Test inhibitory compounds are added to a final concentration of between 1 mM and 10 mM, and the percentage inhibition ascertained by comparison with a control in which no test inhibitor is present.

---

We claim:

1. A substantially pure MurA protein from *Streptococcus pneumoniae* having the amino acid sequence which is SEQ ID NO: 2.

2. A method for identifying inhibitory compounds of *Streptococcus pneumoniae* MurA protein activity, comprising the steps of:
   a) admixing in a suitable reaction buffer
      i) a substantially pure MurA protein as claimed in claim 1;
      ii) a suitable substrate;
      iii) a test inhibitory compound;
   b) measuring by any suitable means an amount of product formed; and
   c) comparing the amount of product formed at step (b) with a control reaction, said control reaction comprising steps (a)(i), (a)(ii), and (b) and wherein said control reaction lacks said test inhibitory compound.

3. A method, as in claim 2 wherein the substrate of step (a)(ii) comprises UDP-GlcNAc and PEP.

4. A method, as in claim 2 wherein the amount of product formed at step (b) is determined by measuring the amount of inorganic phosphate released.

5. A kit useful for identifying inhibitors of stem peptide biosynthesis said kit comprising:
   a) a substantially pure MurA protein, as claimed in claim 1; and
   b) a suitable substrate for said protein.

* * * * *